(12) United States Patent
Yachia et al.

(10) Patent No.: US 9,333,102 B2
(45) Date of Patent: May 10, 2016

(54) STENT

(75) Inventors: Daniel Yachia, Herzliya Pituach (IL); Ronnie Levy, Zur Yigal (IL)

(73) Assignee: ALLIUM MEDICAL SOLUTIONS LTD., Caesarea Industrial Park-South (IL)

(*) Notice: Subject to any disclaimer, the term of this patent is extended or adjusted under 35 U.S.C. 154(b) by 301 days.

(21) Appl. No.: 10/370,592

(22) Filed: Feb. 24, 2003

(65) Prior Publication Data

US 2004/0167635 A1  Aug. 26, 2004

(51) Int. Cl.
*A61F 2/04* (2013.01)
*A61F 2/90* (2013.01)
*A61F 2/92* (2013.01)
*A61F 2/30* (2006.01)

(52) U.S. Cl.
CPC ... *A61F 2/90* (2013.01); *A61F 2/92* (2013.01); *A61F 2002/047* (2013.01); *A61F 2002/30199* (2013.01); *A61F 2210/0014* (2013.01); *A61F 2230/001* (2013.01); *A61F 2230/0023* (2013.01); *A61F 2230/0054* (2013.01); *A61F 2230/0063* (2013.01)

(58) Field of Classification Search
CPC ............... A61F 2002/047; A61F 2002/30121; A61F 2002/30156; A61F 2230/0023; A61F 2230/0086; A61F 2230/0089
USPC ......... 623/1.27–1.3, 1.37, 23.64–23.66, 23.7, 623/1.15; 604/8
See application file for complete search history.

(56) References Cited

U.S. PATENT DOCUMENTS

| | | | | |
|---|---|---|---|---|
| 4,893,623 A | * | 1/1990 | Rosenbluth | 606/192 |
| 5,037,392 A | * | 8/1991 | Hillstead | 606/194 |
| 5,269,802 A | * | 12/1993 | Garber | 623/1.15 |
| 5,320,100 A | * | 6/1994 | Herweck et al. | 600/431 |
| 5,334,217 A | * | 8/1994 | Das | 606/213 |
| 5,411,550 A | * | 5/1995 | Herweck et al. | 623/1.27 |
| 5,522,881 A | * | 6/1996 | Lentz | 623/1.13 |
| 5,639,277 A | * | 6/1997 | Mariant et al. | 606/191 |
| 5,795,318 A | * | 8/1998 | Wang et al. | 604/8 |
| 5,849,037 A | * | 12/1998 | Frid | 623/1.2 |
| 5,855,597 A | * | 1/1999 | Jayaraman | 623/1.16 |
| 5,902,317 A | * | 5/1999 | Kleshinski et al. | 623/1.18 |
| 5,922,019 A | * | 7/1999 | Hankh et al. | 623/1.13 |
| 5,927,345 A | * | 7/1999 | Samson | 138/127 |
| 5,968,070 A | * | 10/1999 | Bley et al. | 606/198 |

(Continued)

FOREIGN PATENT DOCUMENTS

| | | | | |
|---|---|---|---|---|
| CA | 2 358 521 | * | 7/2000 | A61F 2/24 |
| DE | 43 39 265 A1 | * | 5/1995 | A61F 2/02 |

(Continued)

OTHER PUBLICATIONS

Google english translation of DE 43 39 265 A1, from http://www.google.com/patents/DE4339265A1?cl=en[Aug. 20, 2015 12:59:00 PM] printed on Aug. 20, 2015.*

(Continued)

*Primary Examiner* — Thomas J Sweet
*Assistant Examiner* — Cheryl Miller
(74) *Attorney, Agent, or Firm* — Oliff PLC

(57) ABSTRACT

A stent with at least one cross-section having either a vertex or having first and second contour points where the radius of curvature of the first point is at least 2.5 times the radius of curvature of the second point.

23 Claims, 6 Drawing Sheets

(56) References Cited

U.S. PATENT DOCUMENTS

| | | | |
|---|---|---|---|
| 6,071,305 A * | 6/2000 | Brown et al. | 623/1.43 |
| 6,074,338 A * | 6/2000 | Popowski et al. | 600/3 |
| 6,156,064 A * | 12/2000 | Chouinard | 623/1.44 |
| 6,168,610 B1 | 1/2001 | Marin et al. | |
| 6,171,338 B1 * | 1/2001 | Talja et al. | 623/1.22 |
| 6,325,824 B2 * | 12/2001 | Limon | 623/1.2 |
| 6,458,153 B1 * | 10/2002 | Bailey et al. | 623/1.24 |
| 6,572,646 B1 * | 6/2003 | Boylan et al. | 623/1.12 |
| 6,602,272 B2 * | 8/2003 | Boylan et al. | 606/200 |
| 6,626,937 B1 * | 9/2003 | Cox | 623/1.18 |
| 6,656,146 B1 * | 12/2003 | Clayman et al. | 604/8 |
| 6,709,465 B2 * | 3/2004 | Mitchell et al. | 623/23.7 |
| 6,733,536 B1 * | 5/2004 | Gellman | 623/23.66 |
| 6,740,093 B2 * | 5/2004 | Hochschuler et al. | 606/94 |
| 6,790,223 B2 * | 9/2004 | Reever | 623/1.12 |
| 7,128,755 B2 * | 10/2006 | Su et al. | 623/1.15 |
| 7,128,758 B2 * | 10/2006 | Cox | 623/1.19 |
| 2001/0010014 A1 * | 7/2001 | Trozera | 623/1.16 |
| 2002/0072788 A1 * | 6/2002 | Hammond et al. | 623/1.11 |
| 2002/0138133 A1 * | 9/2002 | Lenz et al. | 623/1.15 |
| 2002/0151924 A1 * | 10/2002 | Shiber | 606/194 |
| 2002/0177902 A1 * | 11/2002 | Rioux | A61F 2/04 623/23.67 |
| 2002/0179166 A1 | 12/2002 | Houston et al. | |
| 2003/0032976 A1 * | 2/2003 | Boucek | 606/200 |
| 2003/0065381 A1 * | 4/2003 | Solar et al. | 623/1.15 |
| 2003/0083746 A1 * | 5/2003 | Kuslich | 623/17.11 |
| 2003/0093142 A1 * | 5/2003 | Edelman et al. | 623/1.15 |
| 2003/0135268 A1 * | 7/2003 | Desai | 623/1.19 |
| 2003/0153870 A1 * | 8/2003 | Meyer et al. | 604/96.01 |
| 2003/0187498 A1 * | 10/2003 | Bishop | 623/1.16 |
| 2004/0093065 A1 * | 5/2004 | Yachia et al. | 623/1.13 |
| 2004/0127992 A1 * | 7/2004 | Serhan et al. | 623/17.16 |
| 2004/0181277 A1 * | 9/2004 | Furst | 623/1.16 |
| 2004/0193141 A1 * | 9/2004 | Leopold et al. | 604/527 |
| 2005/0171595 A1 * | 8/2005 | Feldman et al. | 623/1.15 |
| 2006/0116547 A1 * | 6/2006 | Whalen et al. | 600/29 |
| 2006/0206213 A1 * | 9/2006 | Hammond | A61F 2/0009 623/23.66 |

FOREIGN PATENT DOCUMENTS

| | | | |
|---|---|---|---|
| EP | 1 254 645 A1 | 11/2002 | |
| JP | 05-212121 | 8/1993 | |
| JP | 2004-524891 A | 8/2004 | |
| WO | WO95/13761 * | 5/1995 | A61F 2/01 |
| WO | WO 02/060350 A1 | 8/2002 | |
| WO | WO 03/099165 A1 | 12/2003 | |

OTHER PUBLICATIONS

Milroy et al., "Anatomical limitations of the prostatic urethra in using cylindrical stents.", Stenting the Urinary System. ISIS Medical Media, 1998. Chapter 42, pp. 319-321.

Partial English language translation of Japanese Office Action, mailed Nov. 4, 2009.

* cited by examiner

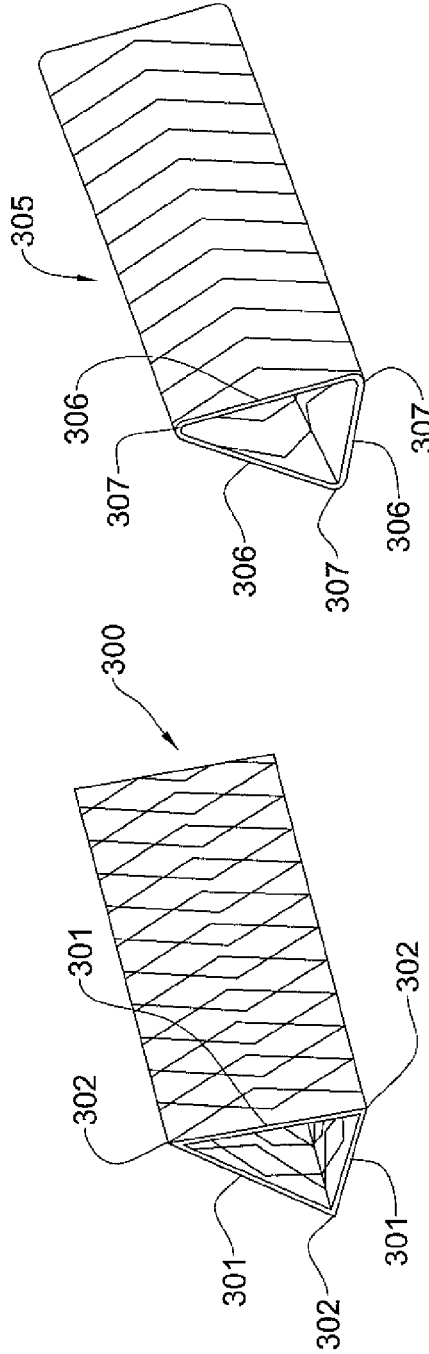
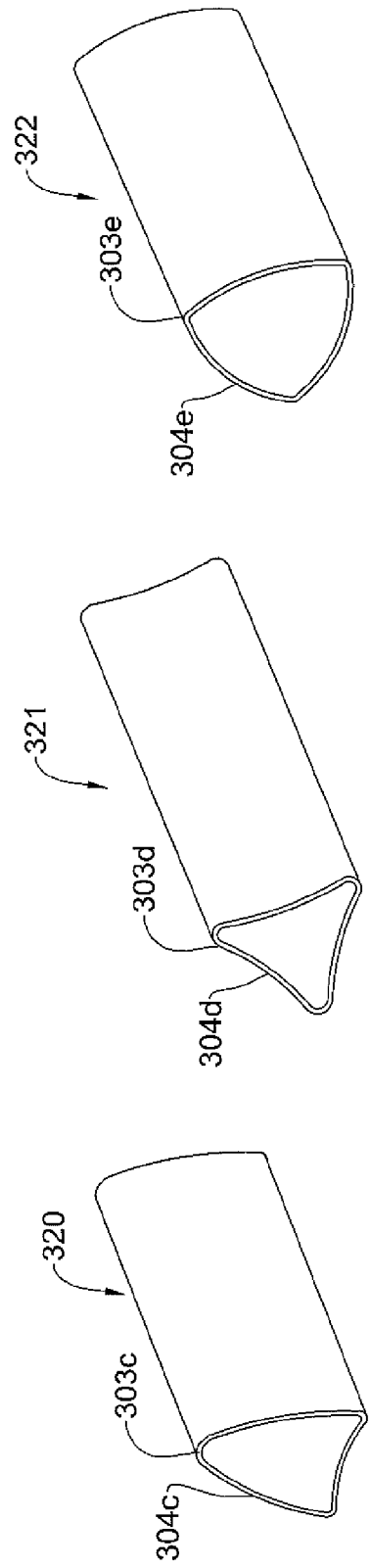
FIG. 3A
FIG. 3B
FIG. 3C
FIG. 3D
FIG. 3E

STENT

FIELD OF THE INVENTION

This invention relates to endoluminal medical devices and more specifically to such devices for maintaining patency of a lumen.

BACKGROUND OF THE INVENTION

Stents are endoluminal devices that are inserted into body lumens and expanded in order to maintain the patency of the lumen. It is known for example, to use a stent to maintain the patency of an artery, a urethra, or a gastrointestinal organ. A temporary stent is left in the lumen for a predetermined period of time, while a permanent stent is intended to remain permanently in the body.

A stent is an elongated device that can exist in two conformations. In the small caliber conformation, the stent is inserted into the body and delivered to the lumen to be treated. Once correctly positioned in the lumen, the stent is deployed by being brought into a large caliber in which it applies radially outward forces against the inner wall of the lumen. The stent is constructed so as to be able to withstand radially inward forces applied to it by the lumen wall, so that the caliber of the stent is maintained after deployment in the lumen.

A stent may be formed, for example, from an elastic material that is unstrained when the stent is in the large caliber conformation. The stent is then mechanically constrained to bring it into the small caliber conformation. This stent may be maintained in the small caliber conformation by inserting it into a restraining sleeve. After positioning in the body, the restraining sleeve is removed. Due to the elastic properties of the stent, the stent spontaneously transforms into the large caliber conformation.

It is also known to form a stent from a material that becomes plastic when strained. The stent is formed in the small caliber conformation in which it is unstrained. A balloon is inserted into the lumen of the stent. The stent is then positioned in the body and the balloon is inflated. This expands the stent into the large caliber conformation by causing a plastic deformation of the stent material.

It is further known to form a stent from a shape memory alloy, such as Nitinol™. A shape memory alloy may exist in two states: a state in which it is super-elastic (the austenitic state) and a state in which it is soft (the martensitic state). The alloy in the austenitic state is formed into a stent in its large caliber conformation. The alloy is then brought into the martensitic state either by cooling the alloy or straining it. In the martensitic state, the alloy is deformed into the small caliber conformation in which it is delivered to the lumen to be treated. After positioning, the alloy is brought into the austenitic state by heating the alloy. In the austenitic state, the stent regains the large caliber conformation due to the shape-memory properties of the alloy.

It is further known to form a stent from a biostable or biodegradable elastic shape memory polymer. The shape memory capability of these polymers allows stents made of these materials to be inserted through small openings and then enlarging their caliber by an increase in temperature. The shape memory effect of polymers is a physical property exhibited best by amorphous polymers whose glass transition temperature is marginally higher than room temperature and whose transition from glass to rubber is particularly sharp. In this case, strain energy can be stored in the polymer by mechanical deformation (e.g. by stretching) followed by cooling. Recovery of the shape memory is exhibited upon reheating the material above the temperature to which it was cooled, allowing a return of the stretched polymer chains to more equilibrium, coiled structures.

In the vascular system a typical stent is about 1.2 times the vessel diameter to ensure appropriate anchoring without causing excessive pressure to the vessel wall. Due to the circular cross-section of the vessel lumen and the stent, after deployment, the entire stent is in contact with the entire surrounding vessel wall. If the wall of the stent is fenestrated, as it expands and presses all around against the vessel wall, some pressure damage to the vessel endothelium occurs. This damage induces a chain tissue reaction until the stent becomes covered with endothelium.

Benign Prostate Hyperplasia (BPH) is the most common tumor affecting human males. As the tumor grows in the prostate, it constricts the prostatic urethral lumen. This constriction reaches a point where the prostatic urethra becomes obstructed, and voiding of urine is inhibited.

There are several methods for treating BPH. The most common treatments include medication to reduce the pressure on the prostatic urethra or reduce the size of the prostate, and in more extreme cases, open or endoscopic surgery, to remove the tumor and widen the prostatic urethra. Surgical BPH treatments typically include open surgery, such as open prostatectomy, and endoscopic surgery such as Transurethral Prostatectomy (TURP), Transurethral Incision of the Prostate (TUIP), and Transurethral Laser or Radiofrequency (RF) vaporization of the prostate. Minimally invasive surgical procedures based on inducing thermal damage to the enlarged prostatic tissues have also been developed. After heating or freezing the prostatic tissue, a scarring process gradually occurs that shrinks the bulk of the tissue, relieving the obstruction.

In all surgical procedures for the treatment of BPH, a catheter is left indwelling in the urethra for a few days. After minimally invasive treatments, many patients often cannot void at all following catheter removal and they must therefore be recatheterized. This is typically due to the continuing oedematous swelling of the tissues. Discomfort can continue for the duration of the natural healing of the wound which may take several weeks. It is well documented that urethral catheters left indwelling more than 48 hours increase the risk of infection, in addition to the discomfort the catheter causes the patient. The infection occurs due to communication between the bladder and the outside world. Bacteria ascends from the urethral opening toward the bladder over the outer surface of the catheter or through its lumen. In such cases, insertion of a temporary sent instead of an indwelling catheter is usually more comfortable for the patient and minimizes the risk of urinary infection.

The use of a temporary stent having a round cross-section that does not conform to the shape of the lumen may cause discomfort and pain to the patient. Some temporary stents used for BPH treatment include an anchor that is connected to the stent by a wire. The stent is deployed in the prostatic urethra, with the anchor positioned in the bulbar urethra, the stent and anchor being connected be a wire through the voluntary urethral sphincter between the prostatic and bulbar urethra that controls the flow of urine from the urinary bladder. This sphincter is a formation of muscle tissue encircling the urethra, contraction of which occludes the urethra to prevent flow of urine from the bladder. Examples of such stents are the Prostakath and the Prostacoil. Other temporary stents, such as the Memokath and the Horizon stent have a bell-shaped end at its sphincteric part for anchoring. Temporary stents without cross-sphincteric parts are more prone to migration It is also known to insert a permanent stent into the prostatic urethra for the treatment of BPH obstructions. Most permanent prostatic stents were originally designed for vascular use and were adopted for prostatic use by mainly changing the caliber and length of the basic design. From among the different vascular stents, the ones that have been used in the urinary tract are the balloon expandable Palmaz stent (marketed as the Titan); the self expanding Strecker, and the Wallstent. The use of the balloon-expandable Palmaz stent was abandoned because of its rigidity, the unacceptably high migration rates of the stent in the urethra, and its inability to become completely embedded into the wall. The braided Wallstent and the knitted Strecker stent have also been used in the urinary tract as permanent stents. However it was the Wallstent which became the most popular permanent stent in urology despite its limitations.

A fenestrated permanent prostatic stent, like a vascular stent, would be expected to react with the urethral tissues, resulting in its becoming embedded in the wall and being covered by a layer of epithelium. However, a prostatic urethral stent does not always become fully embedded in tissue. Milroy and Ng (K. J. Milroy E. J. G., Anatomical limitations of the prostatic urethra in using cylindrical stents. In: Stenting the Urinary System. Ed. D. Yachia. ISIS Medical Media, 1998. Chapter 42. Pages 319-321] studied the failure of permanent prostatic stents to become fully embedded in tissue. They performed 3-Dimensional ultrasonographic scans and found that in BPH the prostatic urethra is deformed by the enlarged prostate lobes and thus does not have a circular cross section. Because of the non-circular cross-section of the prostatic urethra, the tissue coverage of the stent in many cases is not complete. The uncovered, bare wires that remain in constant contact with urine become gradually covered by urinary salts and cause stone development and infection.

FIG. 1 shows schematically views of the lumen of the prostatic urethra in different individuals as might be observed, for example, by an endoscope inserted in the urethra. In FIG. 1a, a prostatic urethra is represented whose lumen 105 has a so-called "A" shaped cross section. In FIG. 1b, a prostatic urethra is represented whose lumen 110 has a so-called "J" shaped cross section. In FIG. 1c, a prostatic urethra is represented whose lumen 100 has a circular or, so-called "O" shaped, cross section.

FIG. 2 shows schematic views of the lumens shown in FIG. 1 after deployment of a stent 200. In FIGS. 2a and b, a stent 200 was deployed in the lumens 105 and 110, respectively. However, since the lumens 105 and 110 did not have an O shape prior to deployment of the stent 200, regions 210 of the outer surface of the stent 200 are not in contact with the wall 205 of the urethra. Under these anatomical conditions, some regions 210 of the permanent stent will not become covered by epithelium. In FIG. 2c, a stent 200 having a circular cross section was deployed in the lumen 100. In contrast to FIGS. 2a and 2b, since the lumen 100 had an O shape prior to deployment of the stent 205, the entire outer surface of the stent 200 is substantially in contact with the wall 205 of the urethra. The entire stent 200 in FIG. 2c can thus be expected to become covered by epithelium.

SUMMARY OF THE INVENTION

The present invention provides a stent for insertion into a region of a body lumen having a non-circular cross section. In accordance with the invention, the stent has at least one cross section in which either (a) there is a vertex or (b) there is at least one pair of points on the contour of the cross-section where the radius of curvature at one of the points in the pair is 2.5 times the radius of curvature of the other point of the pair. As used herein, the term "vertex" denotes a point on the boundary of a cross-section where the boundary has an abrupt change in direction. A vertex may thus be a common endpoint of two con-collinear line segments, or the common endpoint of two curves, or a curve and a line segment. A stent in accordance with the invention may thus have, for example, a closed triangular, polygonal, crescent or hourglass cross-sectional shape. The stent may alternatively have an open triangular polygonal cross section, such as a "V" shaped cross section.

A stent having at least one vertex in a cross-section may be configured to conform to a lumen having a non-circular cross-sectional shape better than a stent having a circular cross-sectional shape. For example, a stent in accordance with the invention having a triangular cross-sectional shape conforms to most of the cross-sectional shape of the prostatic urethra in BPH, better than a stent having a circular cross-section. The triangular cross-section maximizes patient comfort by conforming to the A or I prostate lumenal shapes while maintaining a relatively large and effective opening for urine flow.

The stent may be formed from any material known in the art for manufacturing stents, and includes, elastic materials, plastics and shape-memory alloys and polymers. Furthermore, any device or method known in the art for delivering a stent to the site of its deployment and for expanding a stent may be used with the stent of the invention. In accordance with another of its aspects, the invention provides a stent and a device for deploying the stent in a body lumen.

A stent of the invention may be a permanent stent or a temporary stent. In the case of permanent stent, in a preferred embodiment, the stent is fenestrated so that after deployment in the lumen, it becomes embedded in the epithelium. The stent may be formed, for example, from a mesh material or from a wire. In the case of a prostatic urethral stent, for example, a stent having an expanded cross-sectional shape that is triangular, conforms to the A or I shaped prostatic urethral lumen, so that the entire surface of the stent contacts the surrounding tissues. This contact causes the chain tissue reaction until the stent becomes essentially completely covered by tissue. The bladder neck end of a prostatic urethral stent is preferably angled to conform to the urethral/bladder neck angulation so that the stent becomes embedded in epithelium also in the bladder neck.

The stent may optionally have an anchoring segment to prevent its migration after deployment. The anchor can have any shape including an inverted conical shape. In the case of a permanent stent, the anchor, and can be attached to the stent through a temporary or releasable attachment, such as a retrievable suture, or dissolving sutures, e.g., cat-gut or MONOCRYL® from Ethicon. These dissolving mechanisms, for example, can be such that they dissolve within 10-50 days post deployment, allowing for self anchoring of the permanent segment of the stent by becoming covered by urethral epithelium.

A temporary stent of the invention may optionally be attached to a lumenal lining at one or both of its ends. The term "lumenal lining" is used herein to denote a hollow cylindrical elastic structure that is inserted into a body lumen and that conforms to the shape and caliber of the lumen as the shape and caliber of the lumen change. A lumenal lining for deployment with a stent is disclosed in Applicant's co-pending U.S. Patent application filed on Nov. 13, 2002 entitled "Endolumenal lining". The lining has an unstrained caliber equal to, slightly larger, or slightly smaller than the caliber of the lumen where it is to be deployed. The surface of the lining may be continuous, for example, either by embedding elastic elements of the lining in a flexible material or covering the elastic elements in a flexible sheath.

Use of the stent of the invention in conjunction with a lining has several advantages. First, use of lining adjacent to a stent of the invention eliminates the sharp pressure gradient that otherwise exists on the lumen wall around the ends of the stent. A region of a steep pressure gradient is known to induce ingrowth of tissue at the ends of a stent that partially or completely occludes the lumen at the ends of the stent.

Using a lumenal lining with a stent of the invention is also advantageous when the stent is to be deployed near a sphincter. The stent is positioned in the lumen with the lining intervening between the stent and the sphincter. The lining and the stent may be fabricated as a single unit or may be formed as two separate units that are joined together before insertion into the urethra and inserted together as a single integral unit, or the lining and stent may be inserted separately. The stent maintains the patency of the lumen in a region that is separated from the sphincter by the lining. When the sphincter contracts and the diameter of the lumen adjacent to the sphincter decreases, the diameter of the lining also decreases while conforming to the shape of the lumen wall. When the sphincter relaxes, and the diameter of lumen adjacent to the sphincter increases, the diameter of the lining also increases while conforming to the shape of the lumen wall. The lining thus dynamically conforms to the lumen shape adjacent to the sphincter during opening and closing of the sphincter and prevents reactive proliferative tissue growth at the sphincteric end of the stent. The lining also allows the stent to be more accurately positioned in the lumen near a sphincter. The distance between the sphincter and a region of the prostatic urethra is measured, and a lining is used having a length equal to this distance. The stent and the lining are then positioned as explained above. The presence of the lining near the sphincter also provides some support to the lumen wall adjacent to the sphincter without interfering with the functioning of the sphincter.

The stent may be enclosed in an outer covering material that is made of a biostable, biodegradable or bioabsorbable material, and may contain drugs to prevent excessive tissue proliferation, antibiotics, anti-neoplastic agents or drugs, such as finasteride to reduce an enlarged prostatic mass, in the case of a prostatic urethral stent. For temporary stents, the covering may be made of a biostable material, and for permanent stents, the covering may be made of a biodegradable or bioabsorbable material, which disintegrates within a few days so as to allow the stent to be covered by tissue.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 3a shows a stent having a closed triangular cross-sectional shape in accordance with one embodiment of the invention, FIG. 3b shows a stent having a closed triangular cross-sectional shape in which the vertices are rounded, FIGS. 3c, 3d, and 3e show stents of the invention having a closed triangular cross-sectional shape in which the sides are bent into different configurations.

DETAILED DESCRIPTION OF THE INVENTION

For the sake of convenience and clarity of the description, the invention will be described with reference to a prostatic urethral stent. This is by way of example only, and the stent of the invention may be adapted for use in any body lumen having a non-circular cross-sectional shape.

Figure 3G:
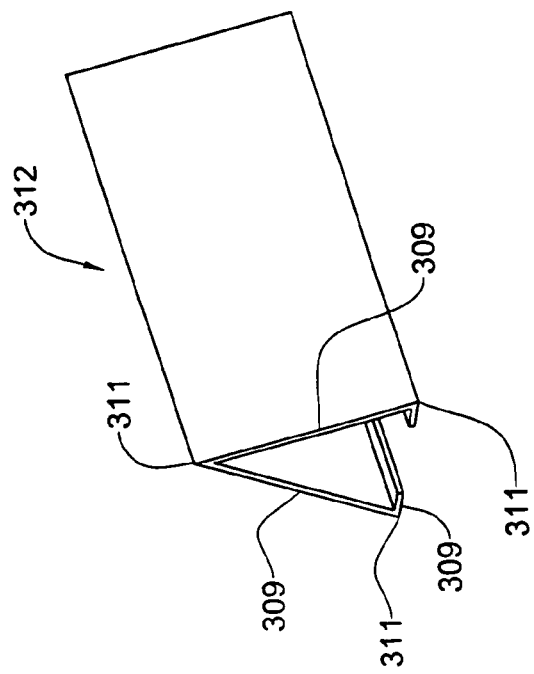
FIGS. 3f and 3g shows stents having open polygonal cross-sectional shapes in accordance with other embodiments of the invention.
Figure 3F:
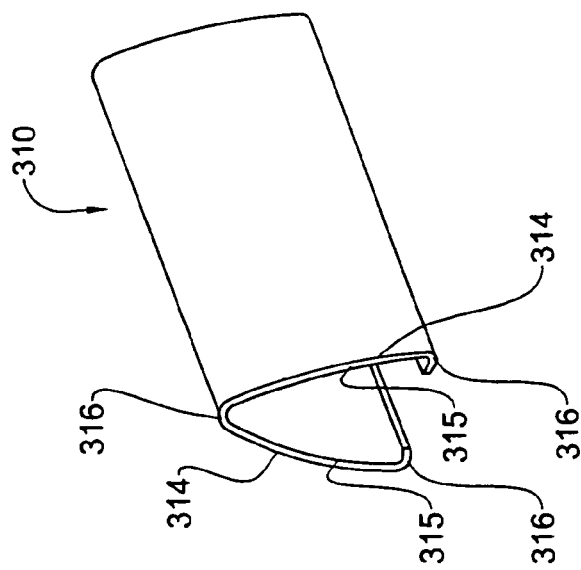

FIG. 3a shows a prostatic lumenal stent 300 having a complete triangular cross-sectional shape. In accordance with the invention, each cross-section of the stent 300 is formed from three line segments 301 that meet at three vertices 302. FIG. 3b shows a second prostatic lumenal stent 305 having a cross section formed by three line segments 306 joined by three arcs 307. Each line segment 306 has an infinite radius of curvature that is clearly more than 2.5 times the radius of curvature at any point on the arcs. FIGS. 3c, 3d, and 3e show three additional prostatic lumenal stents 320, 321, and 322, respectively, having a closed triangular cross-sectional shape in which the sides are bent into different configurations. There is at least one pair of points on each cross section (e.g. the pair of points 303 and 304) where the radius of curvature at one of the points in the pair (e.g. the point 304) is at least 2.5 times the radius of curvature at the other point of the pair (the point 303). FIGS. 3f and 3g show two additional prostatic lumenal stents 310 and 312, respectively, having an incomplete triangular cross-sectional shape. In the stent 312, each cross-section is formed from three line segments 309 and three vertices 311. In the stent 310, each cross-section is formed from two circular or elliptical arcs 314 and three circular arcs 316. The arcs 314 have a maximal radius of curvature (e.g. at the points 315 on the elliptical arcs 314) that is at least 2.5 times radius of the circular arcs 316.

The stent of the invention may be formed from a mesh material so that the stent is fenestrated. As explained above, this allows the stent to become embedded in tissue.

The stent of the invention may be formed from any material known in the art for manufacturing stents, and includes, elastic materials, plastics and shape-memory alloys and polymers. Furthermore, any device or method known in the art for delivering a stent to the site of its deployment and for expanding a stent may be used with the stent of the invention.

Figure 1A:
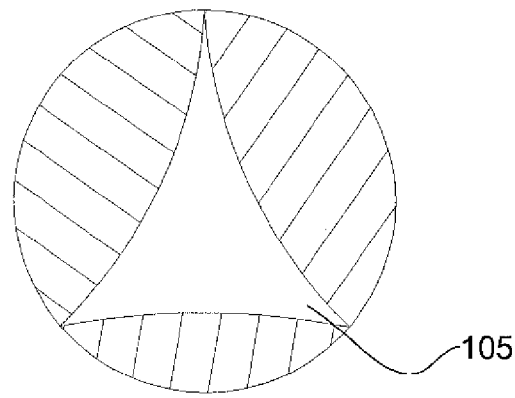
FIGS. 1A-1C shows schematic views of the lumens of prostatic urethras.
Figure 1B:
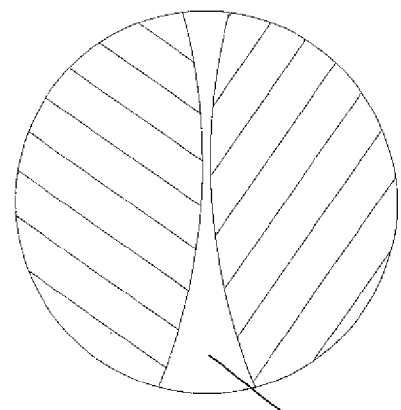
Figure 1C:
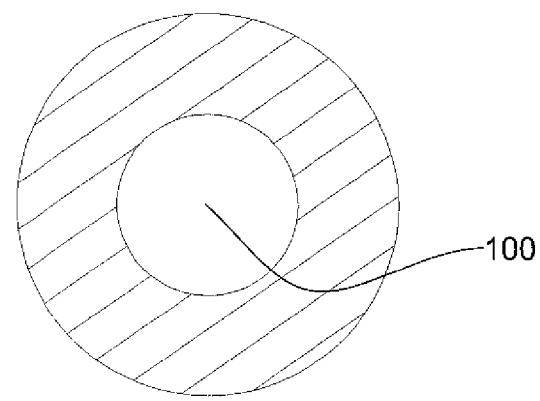
Figure 2A:
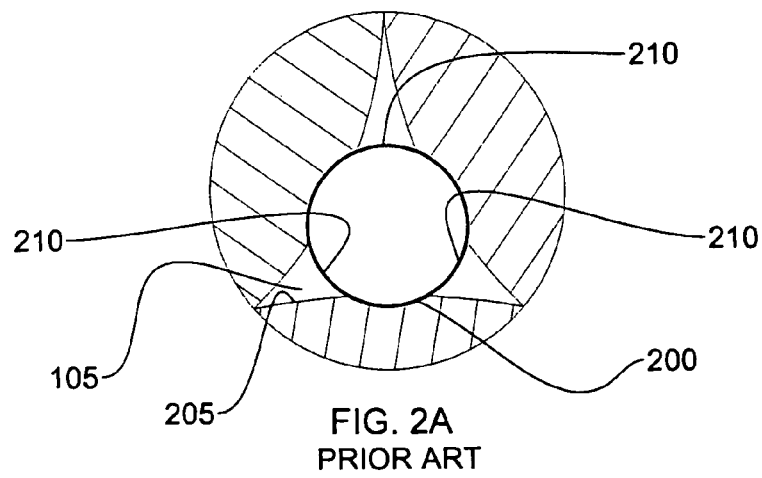
FIGS. 2A-2C shows the lumens of FIG. 1 after deployment of a stent having a circular cross-sectional shape.
Figure 2B:
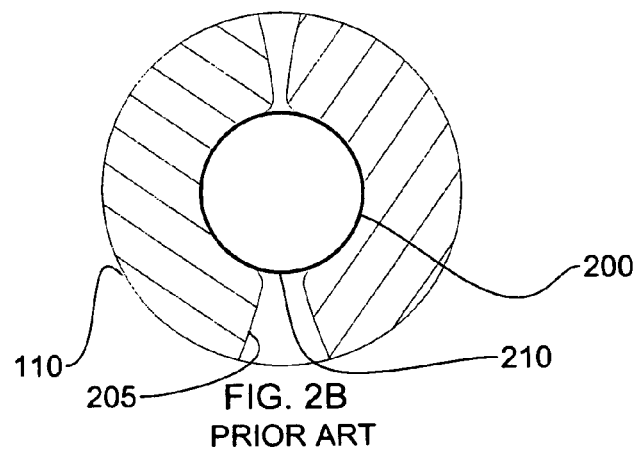
Figure 2C:
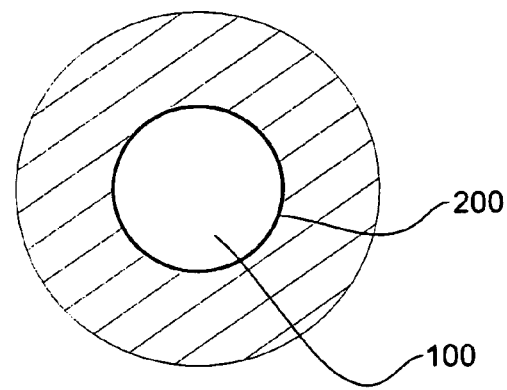
Figure 4A:
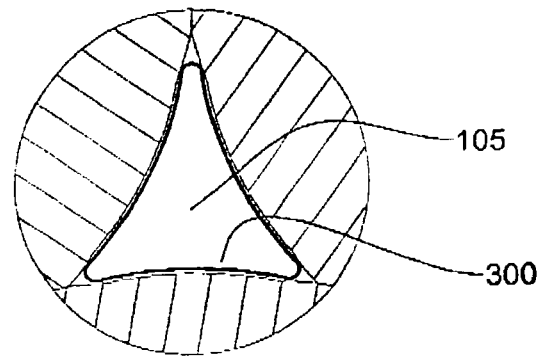
FIGS. 4A-4C shows schematic views of lumens of a prostatic urethra after deployment of a stent in accordance with the invention.
Figure 4B:
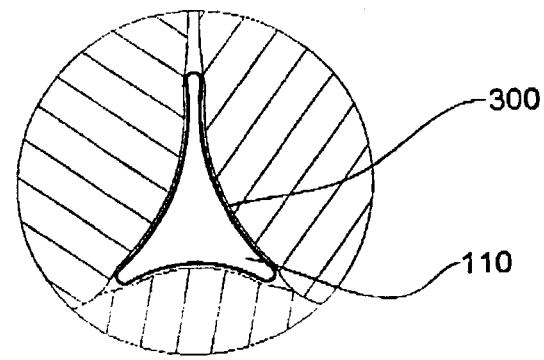
Figure 4C:
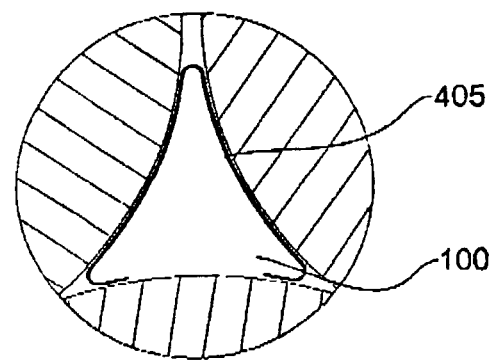

FIG. 4a shows the stent 300 after insertion into the prostatic urethra 105 shown in FIG. 1a ("A" shape prostatic urethra), FIG. 4b shows the stent 300 after insertion into the prostatic urethra 110 shown in FIG. 1b ("I" shape prostatic urethra), and FIG. 4c shows a stent 405 having open polygonal cross-sectional shapes after insertion into the prostatic urethra 100 shown in FIG. 1a ("A" shaped urethra), as might be observed using an endoscope inserted into the urethra. As can be seen, after deployment of the stent 300, the urethral lumens 105 and 110 conform to the shape of the stent 300. This promotes embedding of the stent by tissue growth.

Figure 5:
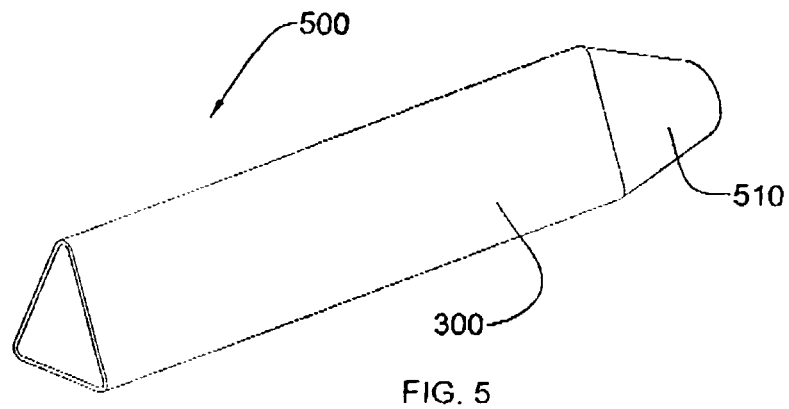
FIG. 5 shows a system comprising a stent of the invention and a lumenal lining.

FIG. 5 shows a system 500 comprising the stent 300 attached to a lumenal lining 510. The lining 510 is dimensioned so as to have an unstrained large caliber that is slightly larger than the maximal caliber prostatic urethra in which it is to be deployed and its shape can be different from the main body shape, for example, the cross section of one end can be triangle as the main body shape and the other end, toward the external sphincter, can be round. The elastic resistance of the lining 510 is less than the radially inward force applied to it by the lumen wall in which it is to be deployed when the lumen constricts. The system 500 is deployed in the urethra with the stent located in the prostatic urethra and the lining adjacent to the external sphincter.

Figure 6A:
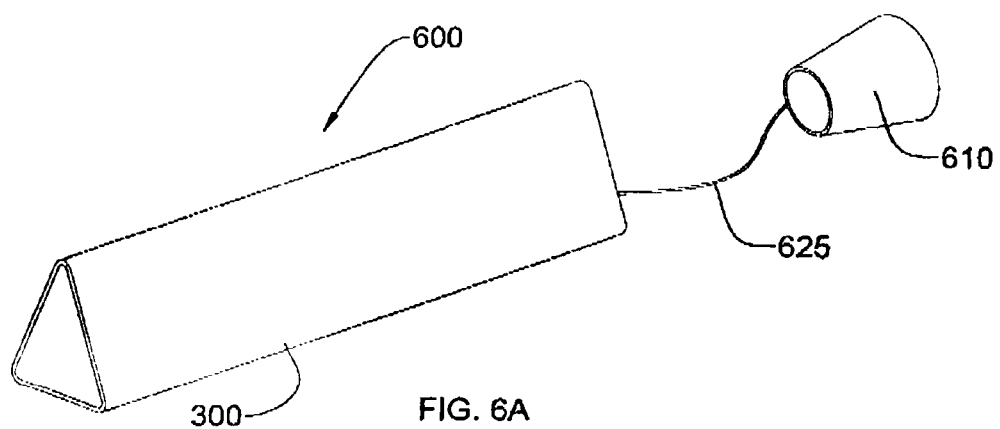
FIG. 6a shows a system comprising a stent of the invention and an anchor.

FIG. 6a shows a system 600 comprising the stent 300 and an anchor 610. The system 600 is deployed in the urethra with the stent 300 in the prostatic urethra and the anchor 610 in the urethra on the opposite side of the external sphincter. The stent 300 and the anchor 610 are joined by a tether 625 that passes through the sphincter after deployment of the system 600. The anchor 610 prevents the stent 300 from migrating away from the prostatic urethra while not interfering with the activity of the sphincter.

Figure 6B:
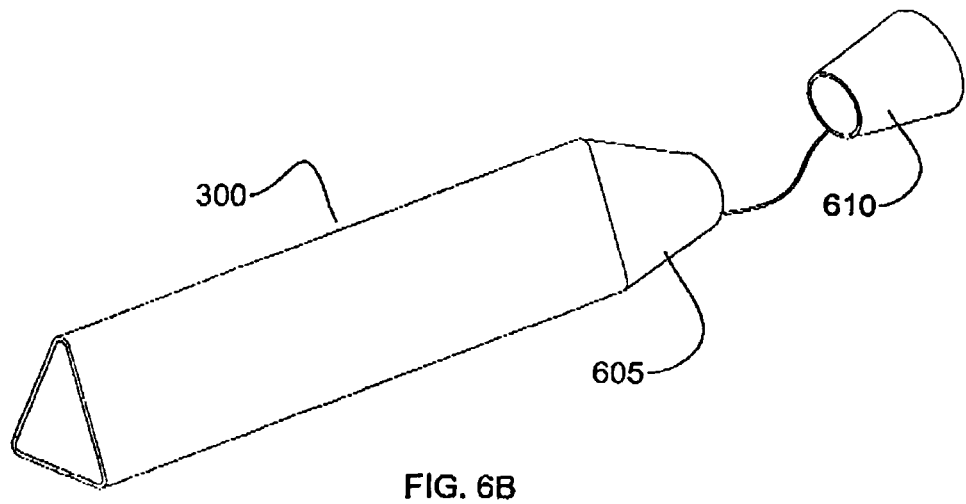
FIG. 6b shows a system comprising a stent of the invention, a lumenal lining, and an anchor.

FIG. 6b shows a system comprising the stent 300 attached to a lumenal lining 605 and the anchor 610.

While the stents described herein have been described for use in the urinary tract, and in particular the male urinary tract, this is exemplary only. These stents could be used in other organs including other tubular organs if modified for the dimensions of and cross sectional shapes of these organs.

The invention claimed is:

1. A stent for insertion into a urethra, the stent comprising:
a generally tubular stent body having a sidewall defining an outer contour and an interior lumen, the generally tubular stent body having a pre-set expanded configuration in which the outer contour is triangular in cross-section when relaxed and free from constraint, the triangular cross-section of the outer contour comprising three sides and three vertices and at least one of the three sides is curved when in the pre-set expanded configuration; wherein:
the generally tubular stent body is collapsible to a collapsed configuration for insertion into the urethra, after which the generally tubular stent body is configured for expansion and reversion back toward the pre-set expanded configuration in the urethra,
the triangular cross-section of the outer contour in the pre-set expanded configuration is configured to conform with a majority of a cross-sectional shape of the urethra when expanded in the urethra, and the interior lumen is configured to concurrently provide a relatively large and effective passageway for urine flow,
the tubular stent body is elongate and having a body length, and
the triangular cross-section of the outer contour includes an opening in one of the three sides in the pre-set expanded configuration, and the opening is continuous along the body length.

2. The stent according to claim 1, wherein the triangular cross-section of the outer contour is a closed triangular cross-section in the pre-set expanded configuration.

3. The stent according to claim 1, wherein the stent is formed from an elastic material, a shape memory alloy, or a shape memory polymer.

4. The stent according to claim 1, wherein the stent is fenestrated.

5. The stent according to claim 1, being a permanent or a temporary stent.

6. The stent according to claim 1, wherein the stent is configured to release one or more substances.

7. The stent according to claim 1, wherein the at least one curved side of the three sides bows inward in the pre-set expanded configuration.

8. The stent according to claim 1, wherein the at least one curved side of the three sides bows outward in the pre-set expanded configuration.

9. The stent according to claim 1, wherein the stent is balloon expandable.

10. The stent according to claim 1, wherein the stent comprises a mesh material.

11. The stent according to claim 1, wherein the triangular cross-section of the outer contour enables the stent to exert radially outward forces against an inner wall of the urethra and is capable of withstanding radially inward forces exerted upon the triangular cross-section by a urethra wall of the urethra.

12. The stent according to claim 1, wherein the one of the three sides having two free edges facing one another and defining the opening.

13. A system for use with a urethra, the system comprising:
a stent for insertion into the urethra, the stent including:
a generally tubular stent body having a sidewall defining an outer contour and an interior lumen, the generally tubular stent body having a pre-set expanded configuration in which the outer contour with is triangular in cross-section when relaxed and free from constraint, the triangular cross-section of the outer contour comprising three sides and three vertices and at least one of the three sides is curved when in the pre-set expanded configuration, and
the generally tubular stent body being collapsible to a collapsed configuration for insertion into the urethra, after which the generally tubular stent body is configured for expansion and reversion back toward the pre-set expanded configuration in the urethra; and
a device configured to deploy the stent, wherein:
the triangular cross-section of the outer contour in the pre-set expanded configuration is configured to conform with a majority of a cross-sectional shape of the urethra when expanded in the urethra, and the interior lumen is configured to concurrently provide a relatively large and effective passageway for urine flow,
the tubular stent body is elongate and having a body length, and
the triangular cross-section of the outer contour includes an opening in one of the three sides in the pre-set expanded configuration, and the opening is continuous along the body length.

14. The system according to claim 13, further comprising a lumenal lining.

15. The system according to claim 14, wherein the lumenal lining is configured to conform to the shape of the urethra as the shape and caliber of the urethra change.

16. The system according to claim 13, further comprising a lumenal anchor.

17. The system according to claim 13, further comprising a lumenal lining, and a lumenal anchor.

18. The system according to claim 17, wherein the lumenal lining is configured to conform to the shape of the urethra as the shape and caliber of the urethra change.

19. The system according to claim 13, wherein the triangular cross-section of the outer contour enables the stent to exert radially outward forces against an inner wall of the urethra and is capable of withstanding radially inward forces exerted upon the triangular cross-section by a urethra wall of the urethra.

20. The system according to claim 13, wherein the one of the three sides having two free edges facing one another and defining the opening.

21. A method of treating a body lumen, the method comprising:
  inserting a stent into the body lumen, the stent including:
    a generally tubular stent body having a sidewall defining an outer contour and an interior lumen, the generally tubular stent body having a pre-set expanded configuration in which the outer contour with is triangular in cross-section when relaxed and free from constraint, the triangular cross-section of the outer contour comprising three sides and three vertices and at least one of the three sides is curved when in the pre-set expanded configuration; wherein:
    the generally tubular stent body is collapsible to a collapsed configuration for insertion into the body lumen, after which the generally tubular stent body is configured for expansion and reversion back toward the pre-set expanded configuration in the body lumen, and
    the body lumen is a urethra.

22. The method according to claim 21, wherein the urethra is a prostatic urethra.

23. The method according to claim 21, wherein the triangular cross-section of the outer contour enables the stent to exert radially outward forces against an inner wall of the body lumen and is capable of withstanding radially inward forces exerted upon the triangular cross-section by a body lumen wall of the body lumen.

\* \* \* \* \*